United States Patent [19]
Martin et al.

[11] Patent Number: 6,013,253
[45] Date of Patent: Jan. 11, 2000

[54] TREATMENT OF MULTIPLE SCLEROSIS USING CONSENSUS INTERFERON AND IL-1 RECEPTOR ANTAGONIST

[75] Inventors: David Martin, Camarillo, Calif.; Norman L. Fischer, Lyons, Colo.

[73] Assignee: Amgen, Inc., Thousands Oaks, Calif.

[21] Appl. No.: 08/911,893

[22] Filed: Aug. 15, 1997

[51] Int. Cl.[7] ........................... A61K 38/21; A61K 38/17
[52] U.S. Cl. ............................ 424/85.7; 424/85.4; 514/2
[58] Field of Search .................................. 424/85.4, 85.7; 514/2

[56] References Cited

U.S. PATENT DOCUMENTS

| | | | |
|---|---|---|---|
| 4,695,623 | 9/1987 | Stabinsky | 530/351 |
| 4,897,471 | 1/1990 | Stabinsky . | |
| 5,075,222 | 12/1991 | Hannum . | |
| 5,372,808 | 12/1994 | Blatt . | |
| 5,541,293 | 7/1996 | Stabinsky . | |

FOREIGN PATENT DOCUMENTS

| | | |
|---|---|---|
| 9173636 | 3/1991 | Australia . |
| 2706772 | 6/1993 | France . |
| WO 91/08285 | 6/1991 | WIPO . |
| WO 91/17184 | 11/1991 | WIPO . |
| WO 92/06707 | 4/1992 | WIPO . |
| WO 92/16221 | 10/1992 | WIPO . |
| WO 93/21946 | 11/1993 | WIPO . |
| WO 94/06457 | 3/1994 | WIPO . |
| WO 94/20122 | 9/1994 | WIPO . |
| WO 94/20517 | 9/1994 | WIPO . |
| WO 94/21235 | 9/1994 | WIPO . |
| WO 94/21275 | 9/1994 | WIPO . |
| WO 95/21629 | 8/1995 | WIPO . |
| WO 96/22793 | 8/1996 | WIPO . |

OTHER PUBLICATIONS

Dhib–Jalbut, S., et al., (1996) *J. IFM Cytokine Res.* 16: 195–200.

Martin, D., et al. (1995) *J. Neuroimmunol.* 61(2): 241–245.

Waksman, et al. *Proc. Soc. Exp. Biol. Med.* "Multiple Sclerosis as a Disease of Immune Regulation" 175:282–294 (1984).

Hafler, et al. *Immunol. Rev.,* "T Cells in Multiple Sclerosis and Inflammatory Central Nervous System Diseases" 100:307–332 (1987).

Rosenberg, et al. "Principles and Applications of Biologic Therapy" in Cancer: *Principles and Practices of Oncology,* 3rd ed.

Balmer *DICP, Ann Pharmacother* "Clinical use of Biologic Response Modifiers in Cancer Treatment" 24: 761–768 (1990).

Ozes et al., *J Interferon Research,* "A Comparison of Interferon–Con 1 . . . " 12:55–59 (1992).

Klein et al., *J. Chromatog.* "Structural Characterization of Recombinant Consensus Interferon–α" 454:205–215 (1988).

Fish et al., *J. Interferon Res.* "The Rode of Three Domains in the Biological Activity of Human Interferon–α" 9:97–114 (1989).

Abreu et al., *Immunol. Commun.,* "Suppression of Experimental Allergic Encephalomyelitis by Interferon" 11: 1–7 (1982).

Abreu et al., *Int. Arch. Allergy Appl. Immunol.,* "Inhibition of Passive Localized Experimental Allergic Encephalomyelitis by Interferon" 72:30–33 (1983).

Johns et al., *Journal Immunol.* "Sucdessful Treatment of Experimental Allergic Encephalomyelitis with Transforming Growth Factor–β11" 147:1792–1796 (1991).

Collins, U.S. Provisional Patent Application No. 60/011,419 (No copy attached).

Collins, et al., U.S. Provisional Patent Application No. 60/032,789 (No copy attached).

*Primary Examiner*—David L. Fitzgerald
*Attorney, Agent, or Firm*—Craig A. Crandall; Ron K. Levy; Steven M. Odre

[57] ABSTRACT

The present invention encompasses methods for preventing and treating multiple sclerosis by administering to patients in need thereof a therapeutically effective amount of IFN-con in combination with IL-1ra.

6 Claims, 7 Drawing Sheets

TREATMENT OF MULTIPLE SCLEROSIS USING CONSENSUS INTERFERON AND IL-1 RECEPTOR ANTAGONIST

The present invention relates to methods for preventing and treating, using consensus interferon (IFN-con), patients suffering from multiple sclerosis (MS).

BACKGROUND OF THE INVENTION

Multiple sclerosis (MS) is an inflammatory demyelinating disease of the central nervous system (CNS), characterized clinically by relapses and remissions, often leading to progressive physical impairment. MS is the most common disabling neurological disorder affecting young white adults. At least 350,000 Americans have MS, with women affected twice as often as men. MS usually starts by the ages of 15 and 50; the average age of onset is 30. The risk of MS varies for different geographical areas and one increases as one lives further north or south of the equator.

The precise etiology and pathogenesis of the disease remain unknown; however, pathologic, genetic, and immunologic features have been identified which suggest that the disease has an autoimmune basis; see e.g., Waksman, et al., *Proc. Soc. Exp. Biol. Med.*, 175:282–294 (1984) and Hafler et al., *Immunol. Rev.*, 100:307–332 (1987). MS follows a varied, often unpredictable course, but is typically categorized into four widely recognized forms: relapsing-remitting (~25% of cases); relapsing-progressive (~40% of cases); chronic-progressive (~15% of cases); and benign (~20% of cases). Nearly all MS patients suffer such symptoms as fatigue, spasticity, tremor, decreased mobility, depression, pain, urologic complications, and cognitive impairment at some point during the course of their disease.

MS is currently incurable, but it is largely treatable. Most treatments are symptomatic; that is, they relieve or prevent a symptom, without being able to repair the underlying defect of demyelination, although corticosteroids and broad immunosuppressants demonstrate transitory, disease-altering benefits. Corticosteroids can reduce the duration of disease flare-ups while some immunosuppressants, e.g., Burroughs-Wellcome's Imuran®, are reputed to lesson the number of such flare-ups experienced by MS patients.

Interferons are a subclass of cytokines that exhibit both antiviral and antiproliferative activity. On the basis of biochemical and immunological properties, the naturally-occurring human interferons are grouped into three classes: interferon alpha (leukocyte), interferon beta (fibroblast) and interferon gamma (immune). Alpha-interferon is currently approved in the United States and other countries for the treatment of hairy cell leukemia, venereal warts, Kaposi's Sarcoma (a cancer commonly afflicting patients suffering from Acquired Immune Deficiency Syndrome (AIDS)), and chronic non-A, non-B hepatitis. Two variants of alpha interferon have received approval for therapeutic use: Interferon alfa-2a, marketed under the trade name Roferon®-A, and Interferon alfa-2b, marketed under the trade name INTRON® A. The amino acid sequences of Roferon®-A and INTRON® A differ at a single position but otherwise are identical to the amino acid sequence of alpha-interferon subtype 2 (subtype A).

In addition to the labeled indications, alpha-interferon is being used or evaluated alone or in conjunction with chemotherapeutic agents in a variety of other cellular proliferation disorders, including chronic myelogenous leukemia, multiple myeloma, superficial bladder cancer, skin cancers (basal cell carcinoma and malignant melanoma), renal cell carcinoma, ovarian cancer, low grade lymphocytic and cutaneous T cell lymphoma, and glioma. Alpha-interferon may be effective in combination with other chemotherapy agents for the treatment of solid tumors that arise from lung, colorectal and breast cancer (see Rosenberg et al. "Principles and Applications of Biologic Therapy" in *Cancer: Principles and Practices of Oncology*, 3rd ed., Devita et al., eds. pp. 301–547 (1989), Balmer *DICP, Ann Pharmacother* 24, 761–768 (1990)).

Type 1 interferons (e.g. interferon alpha and interferon beta) are known to affect a variety of cellular functions, including DNA replication and RNA and protein synthesis, in both normal and abnormal cells. Thus, cytotoxic effects of interferon are not restricted to tumor or virus infected cells but are also manifested in normal, healthy cells as well. As a result, undesirable side effects arise during interferon therapy, particularly when high doses are required. Administration of interferon can lead to myelosuppression resulting in reduced red blood cell, white blood cell and platelet levels. Higher doses of interferon commonly give rise to flu-like symptoms (e.g., fever, fatigue, headaches and chills), gastrointestinal disorders (e.g., anorexia, nausea and diarrhea), dizziness and coughing. It would be useful to reduce or eliminate the undesirable side effects of interferon therapy without diminishing the therapeutic benefits of such therapy.

Betaseron® (Schering Corp's recombinant interferon beta-1b) was the first drug indicated specifically for the treatment of MS. In a major clinical trial, Betaseron® was found to be effective in reducing the number and severity of exacerbations, or relapses, suffered by MS patients, as well as decreasing magnetic resonance imaging (MRI) evidence of MS activity in the brain. Importantly, the results of the trial pertained only to the relapsing-remitting patient group, since other forms of MS were not represented in the trial. Moreover, the trial demonstrated no beneficial effect of the drug on ultimate disability of MS over the 2 to 3 years of the study, and the effectiveness of the drug is significantly impaired by its side effects.

U.S. Pat. Nos. 4,695,623, 4,897,471 and 5,541,293 disclose novel human interferon polypeptides having amino acid sequences which include common or predominant amino acids found at each position among naturally-occurring alpha interferon subtype polypeptides and are referred to as consensus interferons (IFN-con). The IFN-con amino acid sequences disclosed are designated IFN-con$_1$, IFN-con$_2$, and IFNcon$_3$. The preparation of manufactured genes encoding IFN-con and the expression of said genes in *E. coli* are also disclosed. In vitro studies comparing the relative antiviral, antiproliferative, and natural killer cell activities of recombinant IFN-con with either leukocyte or other recombinant type-one interferons demonstrate that IFN-con displays significantly higher activity when compared on a mass basis; Ozes et al., *J Interferon Research*, 12:55–59, 1992.

U.S. Pat. No. 5,372,808 discloses methods of treatment of diseases using consensus interferon. It is shown that IFN-con, when used in the treatment of diseases susceptible to treatment by alpha interferons, does not cause the same degree of side effects in patients as do the alpha interferons. It was further shown that 3 to 5 times higher doses of IFN-con can be used, leading to enhanced therapeutic benefit, with substantially no corresponding increase in the frequency or severity of undesirable side effects.

SUMMARY OF THE INVENTION

The present invention encompasses methods of treatment of multiple sclerosis by administering to patients in need thereof a therapeutically effective amount of IFN-con. The invention is based on the discovery that IFN-con$_1$ was capable of markedly attenuating, in a dose-dependent manner, the clinical severity of EAE after immunization with CNS (guinea pig) homogenate. Moreover, the combination of IFN-con$_1$ with other therapeutics, e.g. IL-1ra, is even more effective in attenuating the clinical signs of EAE.

IFN-con is a nonnaturally-occurring polypeptide having antiproliferative and antiviral activity. Preferably, IFN-con is a polypeptide having the amino acid sequence of IFN-con$_1$, IFN-con$_2$, or IFN-con$_3$. Most preferably, IFN-con has the amino acid sequence of IFN-con$_1$.

It is to be understood that both the foregoing general description and the following detailed description are exemplary and explanatory only and are not restrictive of the invention as claimed.

DETAILED DESCRIPTION OF THE INVENTION

As noted above, the present invention relates to methods for preventing and treating multiple sclerosis in patients suffering therefrom. The method comprises the administration of a therapeutically effective amount of interferon consensus to a patient suffering from MS. In addition, the present invention relates to methods for preventing or treating MS comprising administration of interferon consensus in combination with another active agent, e.g. IL-1ra.

As employed herein, human interferon consensus (IFN-con) means a nonnaturally-occurring polypeptide, which predominantly includes those amino acid residues that are common to a subset of IFN-α's representative of the majority of the naturally-occurring human leukocyte interferon subtype sequences and which includes, at one or more of those positions where there is no amino acid common to all subtypes, an amino acid which predominantly occurs at that position and in no event includes any amino acid residue which is not extant in that position in at least one naturally-occurring subtype. IFN-con encompasses but is not limited to the amino acid sequences designated IFN-con$_1$, IFN-con$_2$ and IFN-con$_3$ which are disclosed in commonly owned U.S. Pat. Nos. 4,695,623, 4,897,471 and 5,541,293, the entire disclosures of which are hereby incorporated by reference. DNA sequences encoding IFN-con may be synthesized as described in the above-mentioned patents or other standard methods.

IFN-con polypeptides are preferably the products of expression of manufactured DNA sequences transformed or transfected into bacterial hosts, especially *E. coli*. That is, IFN-con is recombinant IFN-con. IFN-con is preferably produced in *E. coli* and is purified by procedures known to those skilled in the art and generally described in Klein et al., *J. Chromatog.* 454:205–215 (1988). IFN-con, purified in this manner is reported to have a specific activity of $3 \times 10^9$ units/mg protein as measured in the cytopathic effect inhibition assay using the T98G human cell line; Fish et al. *J. Interferon Res.* 9, 97–114 (1989).

IFN-con may be used alone or in combination with other active agents for the treatment of MS. Active agents contemplated for use are synthetic or natural compounds which demonstrate a biological effect when introduced into a living creature and include peptides, small molecules, carbohydrates, nucleic acids, lipids, and proteins. Proteins contemplated for use include potent cytokines, including various hematopoietic factors such as granulocyte-colony stimulating factor (G-CSF), kerantinocyte growth factor (KGF), stem cell factor (SCF), megakaryocyte growth differentiation factor (MGDF), granulocyte macrophage-colony stimulating factor (GM-CSF), the interferons (alpha, beta, and gamma), the interleukins (2–12), erythropoietin (EPO), fibroblast growth factor (FGF), stem cell factor (SCF), nerve growth factor (NGF), brain-derived neurotrophic factor (BDNF), neurotrophic factor-3 (NT3), platelet-derived growth factor (PDGF), tumor growth factor (alpha, beta), interleukin-1 receptor antagonist (IL-1ra), osteoprotegerin (OPG), glial cell line derived neurotrophic factor (GDNF), p38 inhibitors and obesity protein (OB protein). In a preferred embodiment for treatment of MS, IFN-con is used in conjunction with a therapeutically effective amount of IL-1ra.

Interleukin-1 receptor antagonist (IL-1ra) is a human protein that acts as a natural inhibitor of interleukin-1. Preferred receptor antagonists, as well as methods of making and using thereof, are described in U.S. Pat. No. 5,075,222 (referred to herein as the '222 patent); WO 91/08285; WO 91/17184; AU 9173636; WO 92/16221; WO93/21946; U.S. Provisional Patent Application No. 60/011,419 filed on Feb. 9, 1996 by Collins, entitled on the Provisional Application transmittal letter as "COMPOSITION AND METHOD FOR TREATING INFLAMMATORY DISEASES", U.S. Provisional Patent Application No. 60/032,789 filed on Dec. 6, 1996 by Collins and Bevilacqua, entitled on the Provisional Application transmittal letter as "COMPOSITION AND METHOD FOR TREATING INFLAMMATORY DISEASES"; WO 94/06457; WO 94/21275; FR 2706772; WO 94/21235; DE 4219626, WO 94/20517; and WO 96/22793, the disclosures of which are incorporated herein by reference. The proteins include glycosylated as well as non-glycosylated IL-1 receptor antagonists.

Specifically, three useful forms of IL-1ra and variants thereof are disclosed and described in the '222 patent. The first of these, IL-1raα, is characterized as a 22–23 kD molecule on SDS-PAGE with an approximate isoelectric point of 4.8, eluting from a Mono Q FPLC column at around 52 mM NaCl in Tris buffer, pH 7.6. The second, IL-1raβ, is characterized as a 22–23 kD protein, eluting from a Mono Q column at 48 mM NaCl. Both IL-1raα and IL-1raβ are glycosylated. The third, IL-1raα, is characterized as a 20 kD protein, eluting from a Mono Q column at 48 mM NaCl, and is non-glycosylated. All three of these inhibitors possess similar functional and immunological activities.

Methods for producing IL-1ra are also disclosed in the '222 patent. One disclosed method consists of isolating the IL-1ra from human monocytes, where they are naturally produced. A second disclosed method involves isolating the gene responsible for coding IL-1ra, cloning the gene in suitable vectors and cells types, expressing the gene to produce the inhibitors and harvesting the inhibitors. The latter method, which is exemplary of recombinant DNA methods in general, is a preferred method. Recombinant DNA methods are preferred in part because they are capable of achieving comparatively greater amounts of protein at greater purity. Thus, the invention also encompasses IL-1ra containing an N-terminal methionyl group as a consequence of expression in prokaryotic cells, such as $E.\ coli$.

In general, comprehended by the present invention are pharmaceutical compositions comprising effective amounts of protein or derivative products of the invention together with pharmaceutically acceptable diluents, stabilizers, preservatives, solubilizers, emulsifiers, adjuvants and/or carriers; see, e.g., Remington's Pharmaceutical Sciences, 18th Ed. (1990, Mack Publishing Co., Easton, Pa. 18042) pages 1435–712 which are herein incorporated by reference. An effective amount of active ingredient is a therapeutically, prophylactically, or diagnostically effective amount, which can be readily determined by a person skilled in the art by taking into consideration such factors as body weight, age, therapeutic or prophylactic or diagnostic goal, and release rate desired.

Particularly useful manners of administering the formulations containing IFN-con for systemic delivery are via subcutaneous, intramuscular, intravenous, and intranasal. Also contemplated are intraventricular and intrathecal delivery of IFN-con. Regardless of the manner of administration, the specific dose is calculated according to the approximate body weight of the patient. Further refinement of the calculations necessary to determine the appropriate dosage for treatment is routinely performed by those of ordinary skill in the art and is within the ambit of tasks routinely performed by them without undue experimentation, especially in light of the dosage information and assays disclosed herein. Particularly useful doses of IFN-con in the treatment of MS, e.g., will be in range of 6–15 µg administered subcutaneously three times weekly.

Experimental allergic encephalomyelitis (EAE), a murine model of an autoimmune inflammatory demyelinating disease of the CNS, has been accepted as providing an excellent model to assess interventions to alter the course of human MS. EAE develops in animals injected with spinal cord proteins, and can also be induced by passive transfer of T-cell clones made reactive for certain myelin antigens (e.g. myelin basic protein). Parenteral (IV) natural rat interferon ($10^5$ units) can suppress partially acute EAE in male Lewis rats; Abreu et al., $Immunol.\ Commun.$, 11:1–7 (1982) and inhibit passive hyperacute localized EAE when administered on the same day as immunogen inoculation; Abreu et al., $Int.\ Arch.\ Allergy\ Appl.\ Immunol.$, 72:30–33 (1983). Other parenterally administered cytokines, such as TGF-β can decrease clinical disease and inflammation in brain and spinal cord in EAE; Johns et al., $J.\ Immunol.$, 147:1792–1796 (1991).

In Example 1 provided below, it is shown that IFN-$con_1$ is effective in markedly attenuating, in a dose-dependent manner the clinical severity of EAE after immunization with CNS (guinea pig) homogenate. Example 2 demonstrates that the combination of IFN-$con_1$ with IL-1ra is even more effective in attenuating the clinical signs of EAE, with the associated weight gain improvements appearing to be synergistic. The examples are offered to more fully illustrate the invention but are not to be construed as limiting the scope thereof.

EXAMPLE 1

In this example, it is shown that IFN-$con_1$ is effective in markedly attenuating, in a dose-dependent manner, the clinical severity of EAE after immunization with CNS (guinea pig) homogenate.

A. Product Description

IFN-$con_1$ was produced in $E.\ coli$ using methods described in U.S. Pat. Nos. 4,695,623 and 4,897,471. IFN-$con_1$ was purified by procedures generally described in Klein et al., supra (1988). For subcutaneous administration in the current study, IFN-$con_1$ was supplied as a clear, colorless, sterile protein solution free of particulates and formulated in an aqueous buffer before undergoing sterile filtration and filling the vials. Recombinant IFN-$con_1$ is not less than 95% pure.

B. Model Design

Female Strain 13 guinea pigs (175–200 grams) were anesthetized with 2% isoflurane+$O_2$ and immunized on day 0 with 0.5 mL of an emulsion containing a CNS homogenate of syngenic brain+spinal cord (12 grams) in 24 mL phosphate buffered saline, 24 mL Freund's adjuvant containing 2.5 mg/mL M. Tuberclosis H37Ra (Difco Lab, MI). The emulsion was injected intradermally in 4–5 sites in the neck region of the guinea pigs. All injections of IFN-$con_1$ and vehicle were given subcutaneously and there were several treatment regimens for IFN-$con_1$: 1) treatment (0.01–0.3 mg/kg) began on the day of immunization and continued everyday until day of sacrifice (day 14); 2) treatment (0.01–0.3 mg/kg) began on the day of immunization and continued everyother day until day of sacrifice; 3) treatment (0.3 mg/kg and 0.1 mg/kg) began on day 4 postimmunization and continued everyday until the day of sacrifice; and 4) treatment (1 mg/kg) began on the day of immunization and continued on days 4, 7 and 11 postimmunization.

Evaluation of clinical disease was based on a standard 0–5 scoring system and was conducted everyday over a 14 day period. The spectrum of rating was: 0, normal; 1, hindlimb weakness; 2, paresis in 2 hindlimbs or paralysis in 1 hindlimb; 3, paralysis in both hindlimbs; 4, moribund; and 5, death. Guinea pigs that survived were sacrificed on day 14 and their brain and spinal cord removed for histological examination. The integrated clinical score for each guinea pig over the entire course of the disease was calculated as the area under the curve of daily clinical scores versus time (units arbitrary). The values of the treated groups were compared statistically against those of the vehicle control group using the Mann-Whitney test.

C. Results

The immunization procedure produced clinical signs starting on day 8–10. In general, the severity of the clinical signs increased with time. All vehicle injected animals died by day 11 postimmunization.

Figure 1:
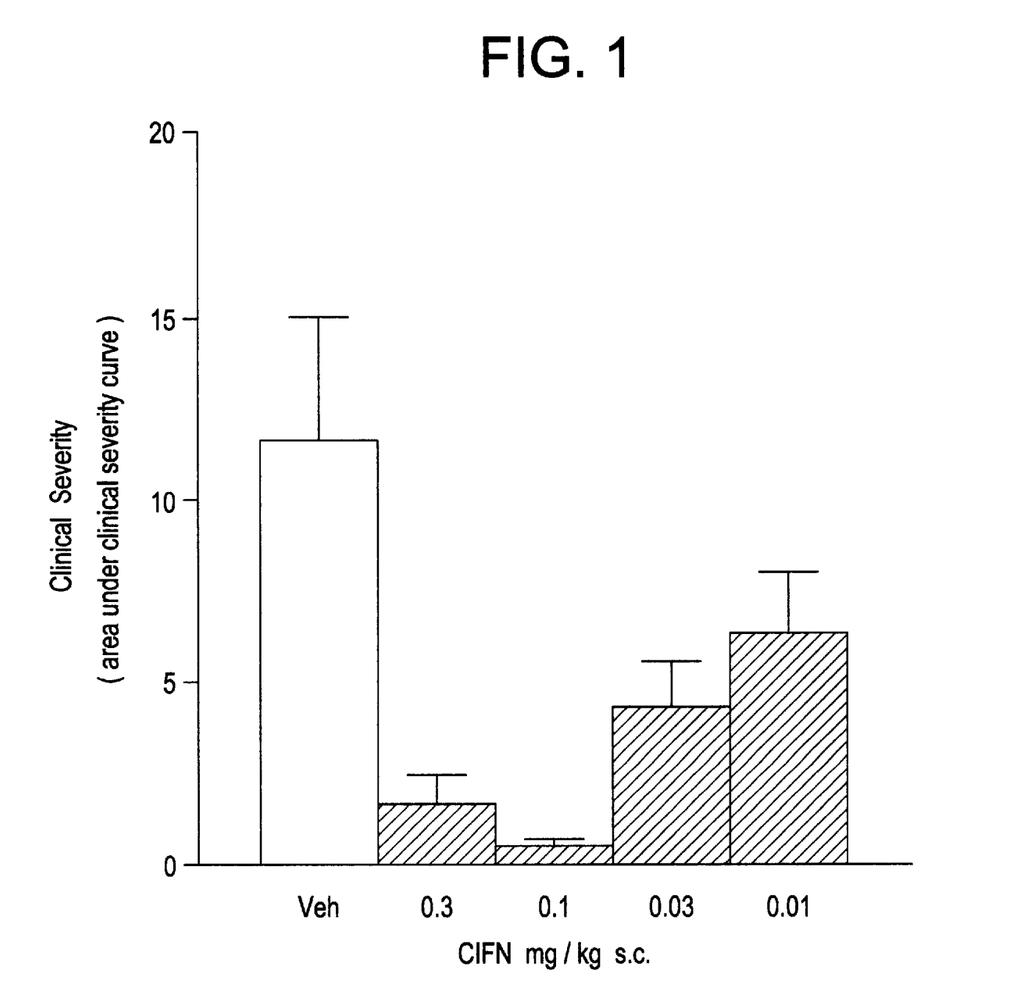
FIG. 1 is a bar graph depicting the effect of everyday dosing of IFN-con starting on day 0 post-immunization on clinical severity in GP EAE. 0.3, 0.1, 0.03 and 0.01 mg/kg IFN-con administered s.c. one time daily is compared against Vehicle after 14 days of treatment.
Figure 2:
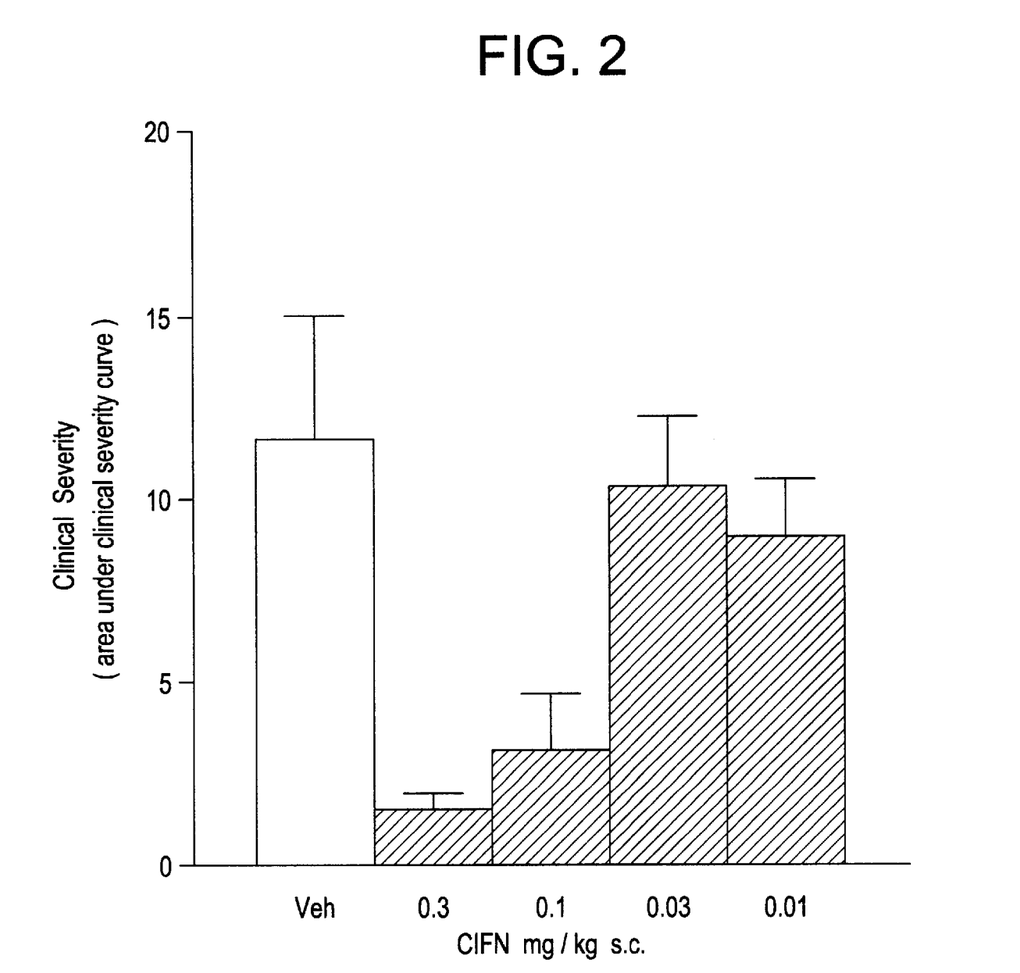
FIG. 2 is a bar graph depicting the effect of everyother day dosing of IFN-con starting on day 0 post-immunization on clinical severity in GP EAE. 0.3, 0.1, 0.03 and 0.01 mg/kg IFN-con administered s.c. one time daily is compared against Vehicle after 14 days of treatment.
Figure 3:
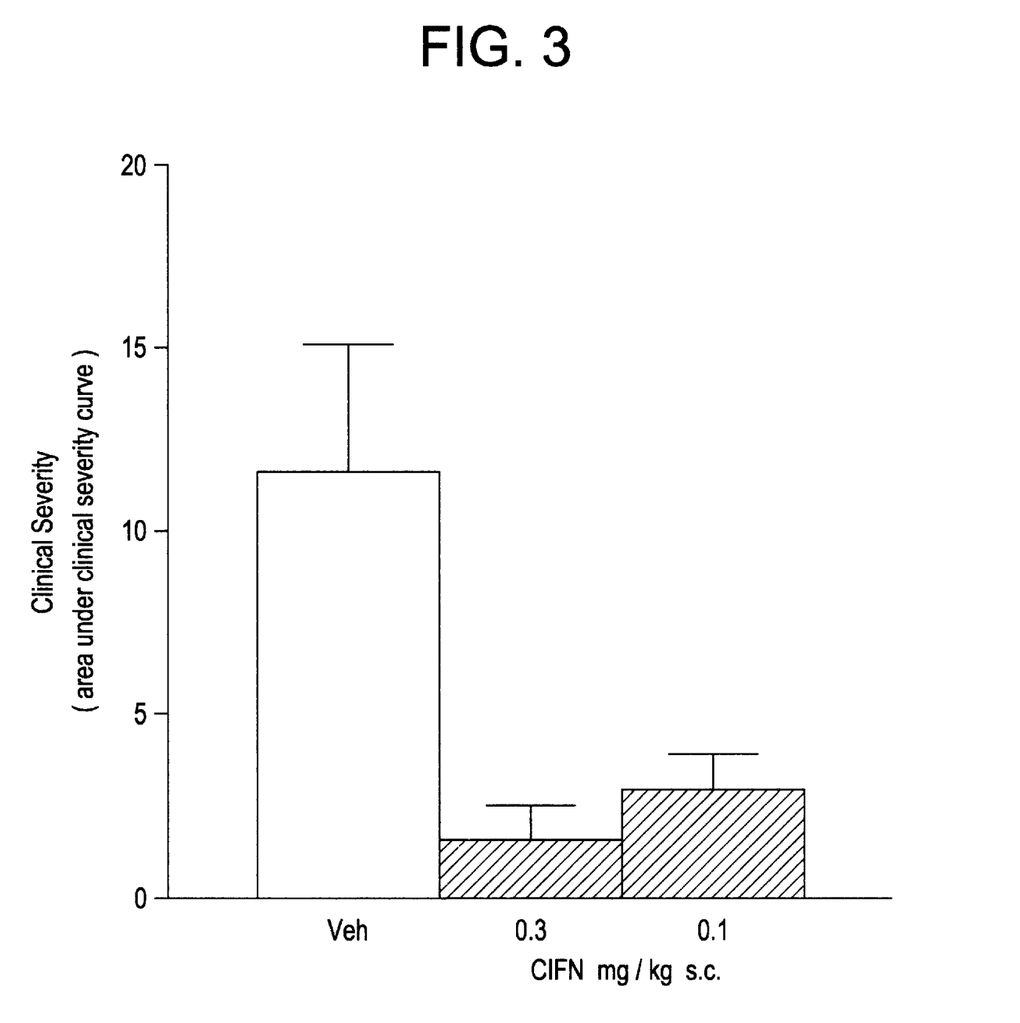
FIG. 3 is a bar graph depicting the effect of everyday dosing of IFN-con starting on day 4 post-immunization on clinical severity in GP EAE. 0.3 and 0.1 mg/kg IFN-con administered s.c. one time daily is compared against Vehicle after 14 days of treatment.
Figure 4:
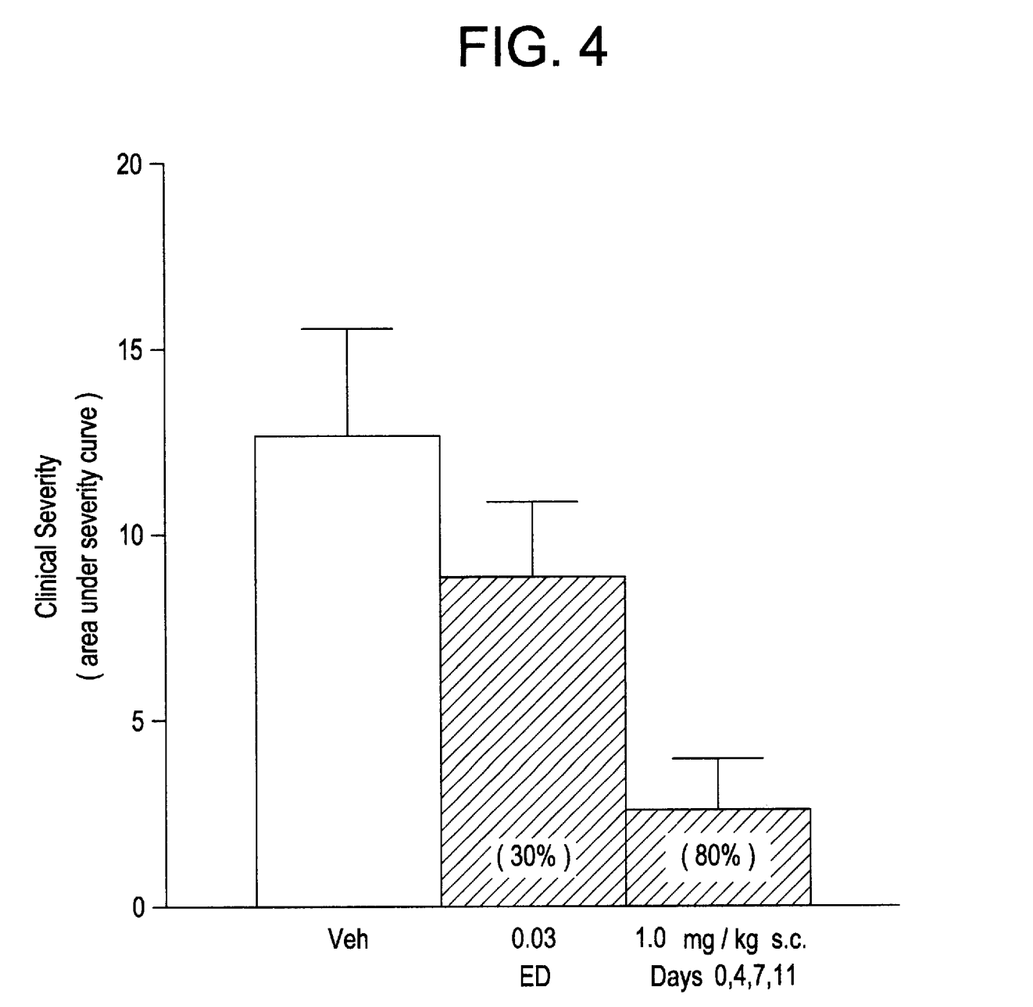
FIG. 4 is a bar graph depicting the effect of day 0, day 4, day 7 and day 11 dosing of 1.0 mg/kg IFN-con vs. everyday dosing of 0.03 mg/kg IFN-con on clinical severity in GP EAE. The IFN-con samples were administered s.c. one time daily and are compared against Vehicle after 14 days of treatment.

As depicted in FIG. 1, IFN-con$_1$ (0.01–0.3 mg/kg s.c.) significantly ($p<0.05$; $p<0.01$) reduced the clinical signs in a dose-dependent manner. This dose-dependent effect was also observed with everyother day dosing regimen (FIG. 2). IFN-con$_1$ (0.3 and 0.1 mg/kg s.c.) dosed everyday starting on day 4 postimmunization significantly ($p<0.01$) attenuated the clinical severity by 87% and 75%, respectively (FIG. 3). IFN-con$_1$ (1 mg/kg s.c.) given on day 0,4,7 & 11 postimmunization significantly ($p<0.002$) attenuated clinical severity by 80% (FIG. 4). Finally, initial examination of animals treated with IFN-con$_1$ showed that the spinal cord tissue had a decrease in the number of inflammatory cells within the CNS as compared to vehicle treated animals.

EXAMPLE 2

In this example, it is shown that combination therapy involving IFN-con$_1$ and IL-1ra is effective in markedly attenuating the clinical severity of EAE after immunization with CNS (guinea pig) homogenate. Moreover, it appears that weight loss caused by treatment with IFN-con$_1$ can be ameliorated by co-administration with IL-1ra.

A. Product Descriptions

IFN-con$_1$ was produced as described in Example 1 above. IL-1ra was produced in *E. coli* using methods such as those described in e.g., U.S. Pat. No. 5,075,222. For subcutaneous administration in the current study, IL-1ra was supplied as a clear, colorless, sterile protein solution free of particulates and formulated in an aqueous buffer before undergoing sterile filtration and filling the vials. Recombinant IL-1ra is not less than 95% pure.

B. Model Design

Female Strain 13 guinea pigs (175–200 grams) were anesthetized with 2% isoflurane+O$_2$ and immunized on day 0 with 0.5 mL of an emulsion containing a CNS homogenate of syngenic brain+spinal cord (12 grams) in 24 mL phosphate buffered saline, 24 mL Freund's adjuvant containing 2.5 mg/mL M. Tuberclosis H37Ra (Difco Lab, MI). The emulsion was injected intradermally in 4–5 sites in the neck region of the guinea pigs. All injections of IFN-con$_1$, vehicle, or IL-1ra were given subcutaneously and there were three treatment regimens utilized: 1) IL-1ra at 100 mg/kg or 10 mg/kg s.c. three times a day starting on day 0 vs. IFN-con$_1$ at 0.03 mg/kg given one time everyday; 2) combination of IL-1ra (100 mg/kg s.c. 3 times/day)+IFN-con$_1$ (0.03 mg/kg s.c. 1 time/day) and IL-1ra (10 mg/kg s.c. 3 times/day)+IFNcon$_1$ (0.03 mg/kg s.c. 1 time/day). The treatment (0.01–0.3 mg/kg) began on the day of immunization and continued everyday until day of sacrifice (day 14). Evaluation of clinical disease was performed as described in Example 1 above.

C. Results

As described in Example 1 above, the immunization procedure produced clinical signs starting on day 8–10. In general, the severity of the clinical signs increased with time. All vehicle injected animals died by day 11 postimmunization.

Figure 5:
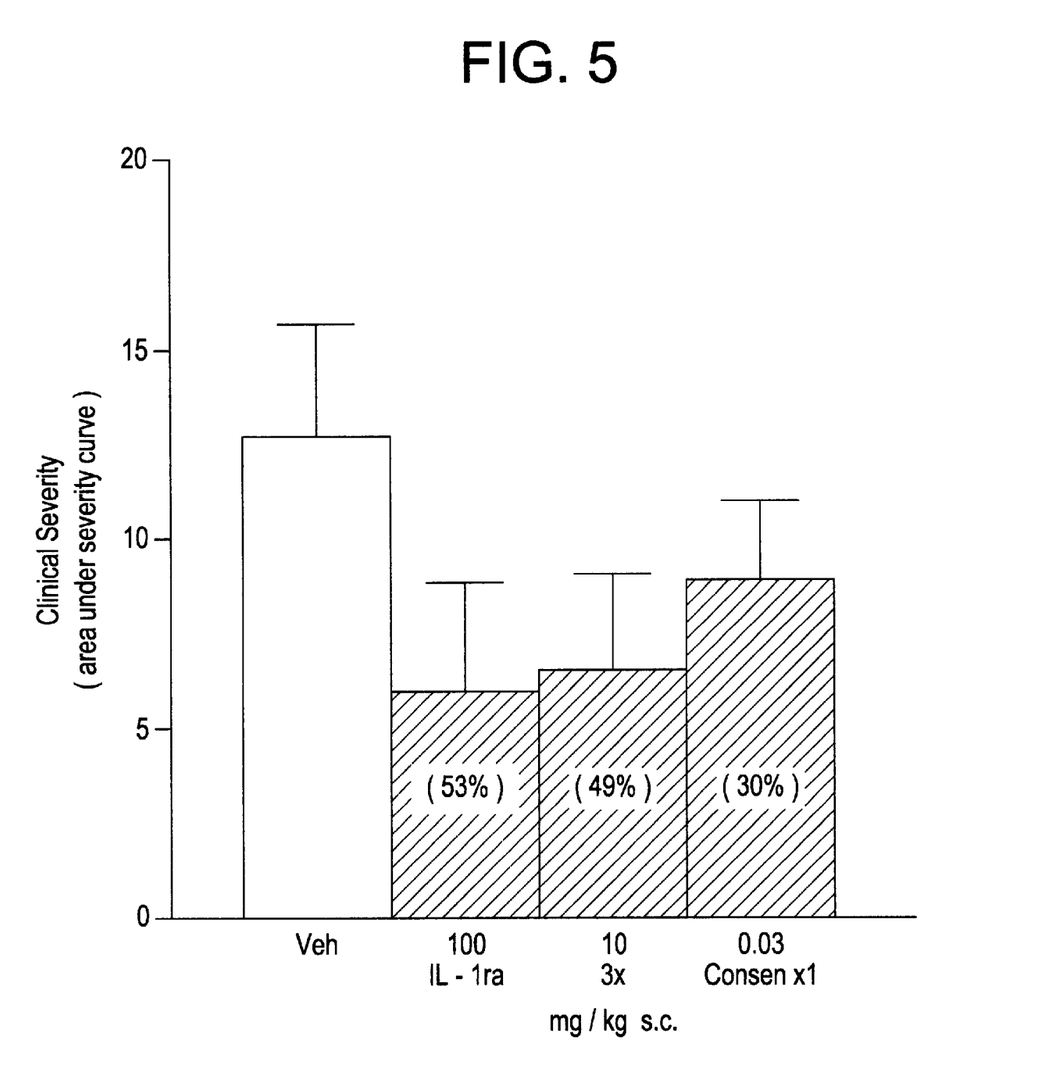
FIG. 5 is a bar graph depicting the effect of everyday dosing of 0.03 mg/kg IFN-con vs. everyday dosing of 100 mg/kg IL-1ra vs. everyday dosing of 10 mg/kg IL-1ra on clinical severity in GP EAE. Dosing started on day 0 post-immunization. IFN-con was administered s.c. one time daily, and IL-1ra administered s.c. 3 times daily. The IFN-con and IL-1ra samples are compared against Vehicle after 14 days of treatment.
Figure 6:
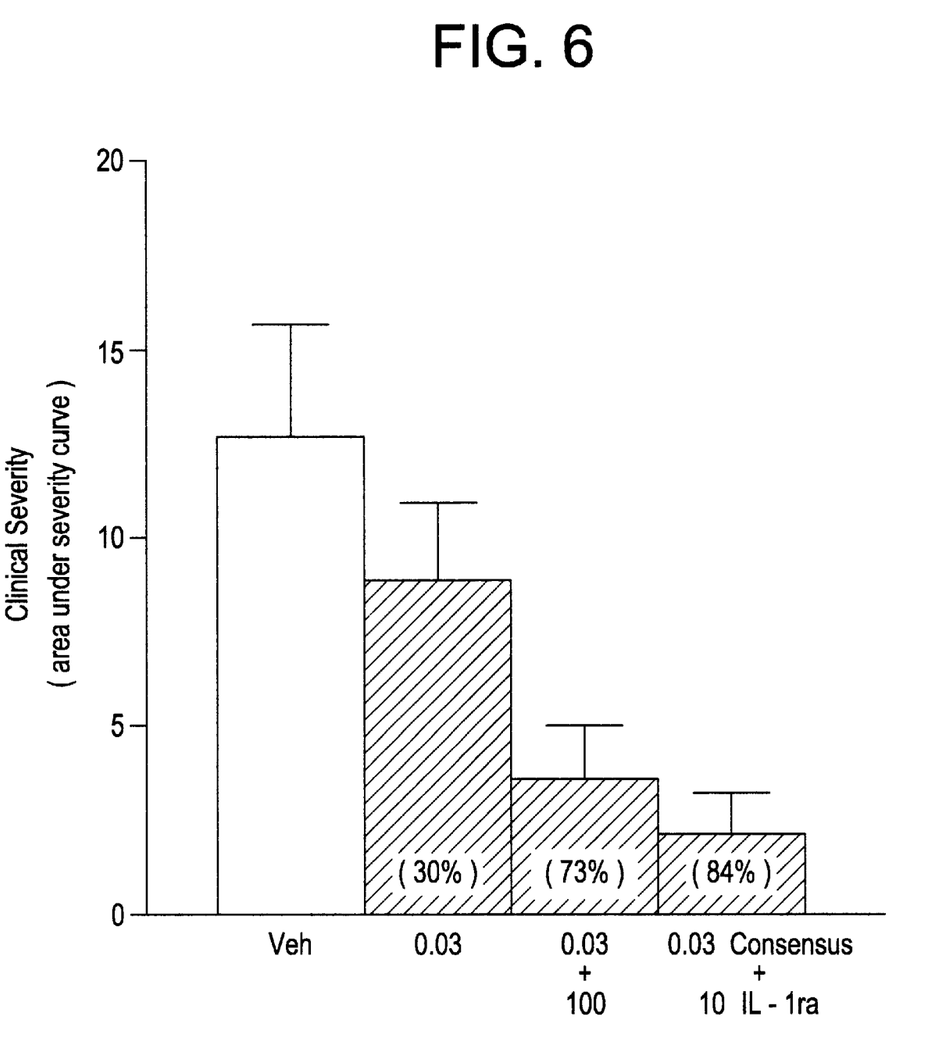
FIG. 6 is a bar graph depicting the effect of IFN-con+IL-1ra combination therapy on clinical severity in GP EAE. IFN-con was administered s.c. one time daily and the IL-1ra administered s.c. three times daily. A combination comprising 0.03 mg/kg IFN-con+100 mg/kg IL-1ra and a combination comprising 0.03 mg/kg IFN-con+10 mg/kg IL-1ra was compared against 0.03 mg/kg IFN-con alone and against Vehicle after 14 days of treatment.
Figure 7:
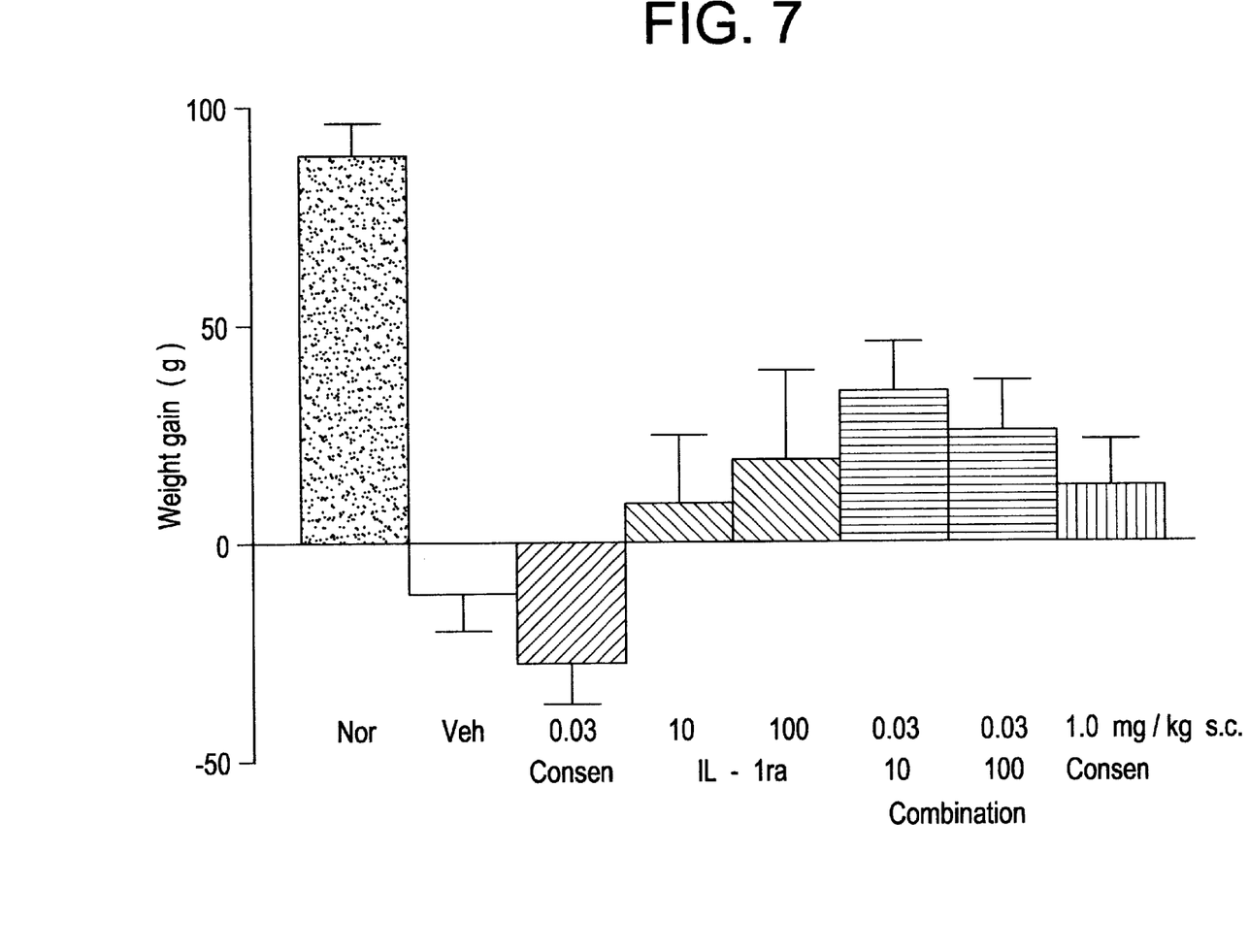
FIG. 7 is a bar graph depicting the effect of IFN-con, IL-1ra, IFN-con+IL-1ra, and Vehicle on weight gain in GP EAE. IFN-con (0.03 and 1.0 mg/kg) was administered s.c. one time daily and IL-1ra (10 and 100 mg/kg) administered s.c. three times daily. A combination comprising 0.03 mg/kg IFN-con+100 mg/kg IL-1ra and a combination comprising 0.03 mg/kg IFN-con+10 mg/kg IL-1ra was also tested and all test samples compared against weight gain in a normal guinea pig after 14 days of treatment.

As depicted in FIG. 5, IL-1ra at 100 mg/kg or 10 mg/kg s.c. three times a day starting on day 0 attenuated the clinical signs by 53% and 49% respectively, as compared to 30% attenuation observed with administration of IFN-con, (0.03 mg/kg s.c. 1 time daily). The combination of IL-1ra (100 mg/kg s.c. 3 times daily+IFN-con$_1$ (0.03 mg/kg s.c. 1 time daily) or IL-1ra (10 mg/kg s.c. 3 times daily+IFN-con$_1$ (0.03 mg/kg s.c. 1 time daily) attenuated the clinical signs by 73% and 84% respectively (FIG. 6). Furthermore, the combinations significantly improved weight gain in the animals as compared to vehicle treated animals (FIG. 7).

What is claimed is:

1. A method for preventing or treating multiple sclerosis which comprises administering to a patient in need thereof a therapeutically effective amount of a combination of consensus interferon (IFN-con) and interleukin-1 receptor antagonist (IL-1ra), wherein the weight loss associated with treatment employing an equivalent amount of IFN-con alone is reduced.

2. A method according to claim 1, wherein said consensus interferon is selected from the group consisting of IFN-con$_1$, IFN-con$_2$, and IFN-con$_3$.

3. A method according to claim 2, wherein said consensus interferon is IFN-con$_1$.

4. A method according to claim 1 wherein said consensus interferon is a product of prokaryotic expression of an exogenous DNA sequence.

5. A method according to claim 1 wherein said consensus interferon and interleukin-1 receptor antagonist are administered in a pharmaceutically acceptable carrier.

6. A method according to claim 1, wherein the therapeutically effective amount is administered orally, intravenously, intramuscularly, subcutaneously, intranasally, intraventricularly, intrathecally, or intralesionally.

* * * * *